(12) United States Patent
Selvaraj et al.

(10) Patent No.: US 11,406,305 B2
(45) Date of Patent: *Aug. 9, 2022

(54) SIGNAL QUALITY METRIC FOR CARDIOVASCULAR TIME SERIES

(71) Applicant: Vital Connect, Inc., San Jose, CA (US)

(72) Inventors: Nandakumar Selvaraj, Santa Clara, CA (US); Ravi Narasimhan, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/022,753

(22) Filed: Jun. 29, 2018

(65) Prior Publication Data

US 2018/0303365 A1 Oct. 25, 2018

Related U.S. Application Data

(63) Continuation of application No. 13/928,652, filed on Jun. 27, 2013, now Pat. No. 10,039,463.

(51) Int. Cl.
*A61B 5/316* (2021.01)
*A61B 5/00* (2006.01)
*A61B 5/0205* (2006.01)
*A61B 5/1455* (2006.01)
*A61B 5/352* (2021.01)

(52) U.S. Cl.
CPC .......... *A61B 5/316* (2021.01); *A61B 5/0006* (2013.01); *A61B 5/0205* (2013.01); *A61B 5/14551* (2013.01); *A61B 5/352* (2021.01); *A61B 5/7203* (2013.01); *A61B 5/7221* (2013.01)

(58) Field of Classification Search
CPC . A61B 5/04012; A61B 5/0006; A61B 5/0205; A61B 5/0456; A61B 5/14551; A61B 5/7203; A61B 5/7221
USPC ........................................................ 600/509
See application file for complete search history.

(56) References Cited

U.S. PATENT DOCUMENTS

| | | | | |
|---|---|---|---|---|
| 2003/0208129 | A1* | 11/2003 | Beker | A61B 5/366 600/509 |
| 2006/0217614 | A1 | 9/2006 | Takala | |
| 2006/0235321 | A1* | 10/2006 | Simske | A61B 5/341 600/512 |
| 2007/0208266 | A1* | 9/2007 | Hadley | A61B 5/349 600/519 |
| 2009/0326356 | A1* | 12/2009 | Kracker | A61B 5/1459 600/522 |

(Continued)

*Primary Examiner* — Mallika D Fairchild
*Assistant Examiner* — Minh Duc G Pham
(74) *Attorney, Agent, or Firm* — Brundidge & Stanger, P.C.

(57) ABSTRACT

A method and system for determining a signal quality metric of a cardiovascular time series utilizing a wireless sensor device are disclosed. In a first aspect, the method comprises determining subsequent values of the cardiovascular time series and comparing the determined subsequent values to a threshold value. In a second aspect, a wireless sensor device comprises a processor and a memory device coupled to the processor, wherein the memory device includes an application that, when executed by the processor, causes the processor to determine subsequent values of the cardiovascular time series and compare the determined subsequent values to a threshold value.

18 Claims, 3 Drawing Sheets

(56) References Cited

U.S. PATENT DOCUMENTS

2012/0016249 A1* 1/2012 Lian .............. A61B 5/349
                                                600/509
2013/0274580 A1* 10/2013 Madsen ........... A61B 5/316
                                                600/365

* cited by examiner

SIGNAL QUALITY METRIC FOR CARDIOVASCULAR TIME SERIES

CROSS-REFERENCE TO RELATED APPLICATION

This application is a Continuation of U.S. application Ser. No. 13/928,652, filed Jun. 27, 2013, entitled "SIGNAL QUALITY METRIC FOR CARDIOVASCULAR TIME SERIES," which is incorporated herein by reference in its entirety.

FIELD OF THE INVENTION

The present invention relates to wireless sensor devices, and more particularly, to determining a signal quality metric for cardiovascular time series utilizing such wireless sensor devices.

BACKGROUND

Wireless sensor devices are used in a variety of applications including cardiovascular health monitoring of patients. In many of these applications, a wireless sensor device is attached directly to the user's skin (e.g. near the chest area) to measure certain data such as cardiovascular time series. Cardiovascular time series are certain physiological signal features used to monitor physiological as well as pathological changes in a variety of patients.

Cardiovascular time series are extracted on a beat-to-beat basis from an electrocardiogram (ECG) signal and on a pulse-to-pulse basis from pulse oximetric photoplethysmogram (PPG) or noninvasive blood pressure waveforms. Motion and noise artifacts corrupt the raw signal waveforms and the derived cardiovascular time series as well. Conventional methods to accurately detect/reduce artifacts suffer from limitations that include not being optimal for in-band noise and prolonged artifact events, failing to preserve absolute time, failing to ensure artifact free in the derived time series, and not being applicable to various types of motion artifacts. Therefore, there is a strong need for a cost-effective and efficient solution that overcomes the aforementioned issues. The present invention addresses such a need.

SUMMARY OF THE INVENTION

A method and system for determining a signal quality metric of a cardiovascular time series utilizing a wireless sensor device are disclosed. In a first aspect, the method comprises determining subsequent values of the cardiovascular time series and comparing the determined subsequent values to a threshold value.

In a second aspect, a wireless sensor device comprises a processor and a memory device coupled to the processor, wherein the memory device includes an application that, when executed by the processor, causes the processor to determine subsequent values of the cardiovascular time series and compare the determined subsequent values to a threshold value.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
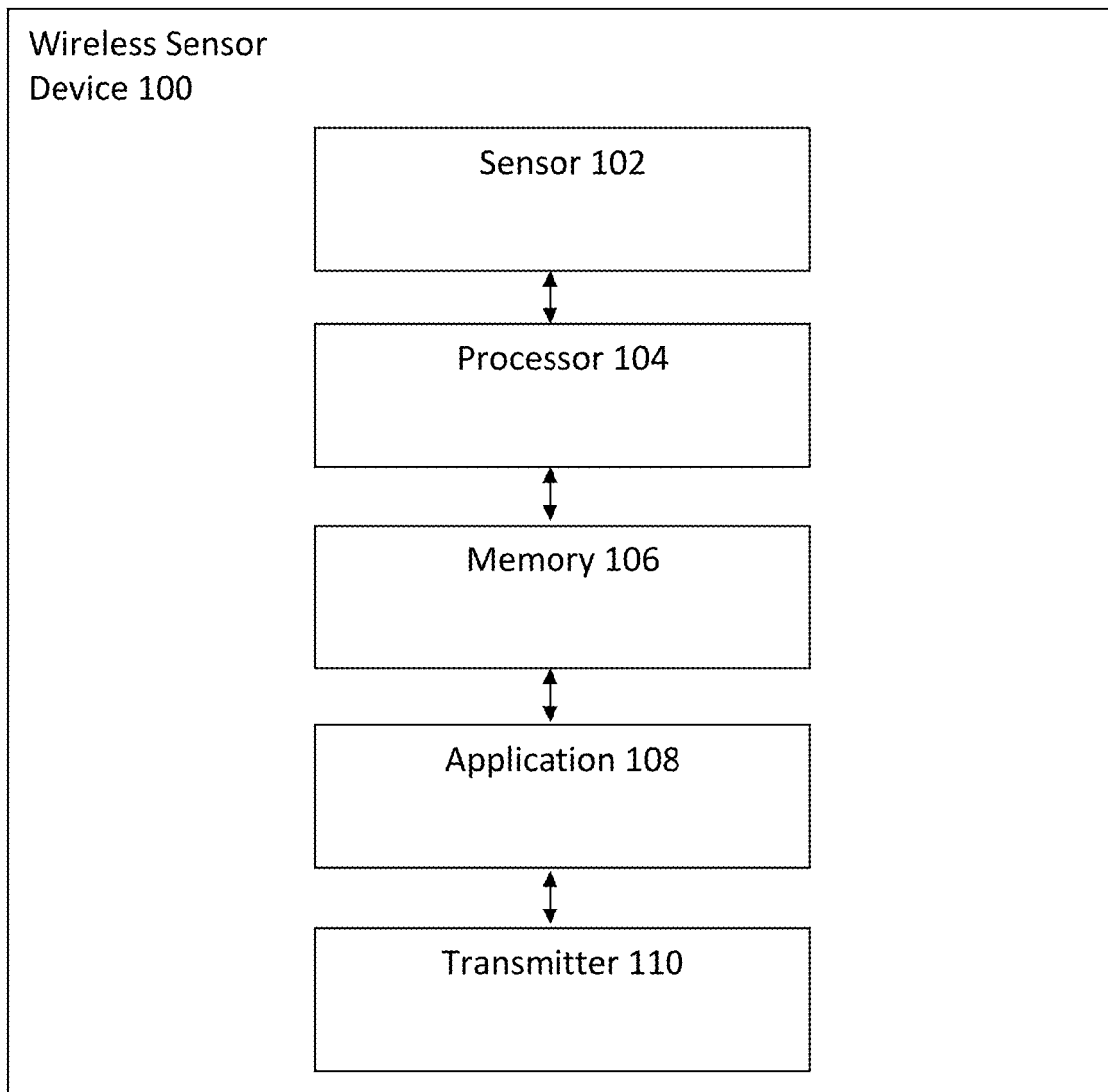
FIG. 1 illustrates a wireless sensor device in accordance with an embodiment.

The present invention relates to wireless sensor devices, and more particularly, to determining a signal quality metric for cardiovascular time series. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

The accurate detection and reduction of motion and noise artifacts in physiological signals detected by a wireless sensor device enables more accurate extraction of cardiovascular time series. In one embodiment, signal processing techniques and motion artifact detection algorithms that identify corrupted signal portions and exclude/delete the corrupted signal portions in subsequent analysis are used to extract the cardiovascular time series. In another embodiment, the effects of motion artifacts are minimized by other signal processing techniques that filter or reconstruct raw waveforms of the physiological signals before extracting the cardiovascular time series.

The aforementioned signal processing techniques are effective for bursts of isolated artifact events that last only a short duration but are not optimal for prolonged artifact events as well as in-band noise artifacts. Additionally, excluding the corrupted signal portions fails to preserve absolute time in the subsequent analysis and signal reconstruction of motion artifact time periods using templates fails to reflect the true dynamics of the physiological signals. The motion artifact detection algorithms also often fail to detect certain physiological artifacts such as ectopic beats.

Accordingly, a method and system in accordance with the present invention determines a signal quality metric that provides concurrent quality assessment and can be utilized for all types of cardiovascular time series generated by a wireless sensor device. An algorithmic process is utilized by a wireless sensor device that has been attached to a user to identify physical and physiological artifacts in the derived cardiovascular time series signals and to provide a concurrent Time Series Signal Quality (TSQ) metric.

Examples of cardiovascular time series derived from ECG signals include RR intervals that provide instantaneous heart rate, QRS amplitude/area that are used as a surrogate respiratory signal, and time intervals such as PR, QRS, and ST. Examples of cardiovascular time series derived from pulse oximetry signals include peak-to-peak (PP) pulse intervals that provide instantaneous pulse rate, systolic pulse amplitude that monitors physiological changes related to oxygen saturation, respiration, and blood volume, and reflection index that measures the vascular stiffness.

Examples of cardiovascular time series derived from noninvasive blood pressure signals include beat-to-beat systolic, diastolic, and mean blood pressure measurements. An example of cardiovascular time series derived from more than one signal include a pulse transmit time that measures vascular stiffness and inspiratory effort and that is obtained as a time difference between the R wave peak ECG to the onset or upstroke of the peripheral pulse waveform.

In one embodiment, the TSQ is derived by a wireless sensor device using a first process algorithm that compares two subsequent beats or cardiac cycles (e.g. N and N+1) for the detection of artifacts with respect to a Threshold Value (TH) which is determined from the signal variability of the cardiovascular time series. In this embodiment, the entire time series data is taken into consideration making the first process more suitable for an offline analysis.

In one embodiment, the TSQ is derived by a wireless sensor device using a second process algorithm that compares three subsequent beats (e.g. N, N−1, N+1) for the detection of artifacts with respect to a Reference Value (Ref) and a Threshold Value (TH). In this embodiment, the Ref is updated based on the time series values of a number of normal consecutive beats or cardiac cycles (Nb) window (e.g. 5 beats) and the TH is a "priori" estimate of the time series variability. The second process is more suitable for real-time or online analysis.

One of ordinary skill in the art readily recognizes that the cardiovascular time series utilized by the wireless sensor device using the first and second processes can be any of the aforementioned examples including but not limited to RR intervals and QRS area and that would be within the spirit and scope of the present invention.

One of ordinary skill in the art readily recognizes that a variety of wireless sensor devices can be utilized to measure the physiological signals utilized to determine the cardiovascular time series and the associated TSQ including but not limited to a wireless sensor device in a patch form-factor, tri-axial accelerometers, uni-axial accelerometers, bi-axial accelerometers, gyroscopes, and pressure sensors and that would be within the spirit and scope of the present invention.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached, in any orientation to a user and on any location of the user. In another embodiment, the wireless sensor device 100 is chest-mounted to the user. The sensor 102 obtains data from the user and transmits the data to the memory 106 and in turn to the application 108. The processor 104 executes the application 108 to monitor physiological signals and derive the TSQ. The information is transmitted to the transmitter 110 and in turn relayed to another user or device.

In one embodiment, the sensor 102 is bipolar electrodes or a microelectromechanical system (MEMS) tri-axial accelerometer and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

To describe the features of the present invention in more detail, refer now to the following description in conjunction with the accompanying Figures.

Figure 2:
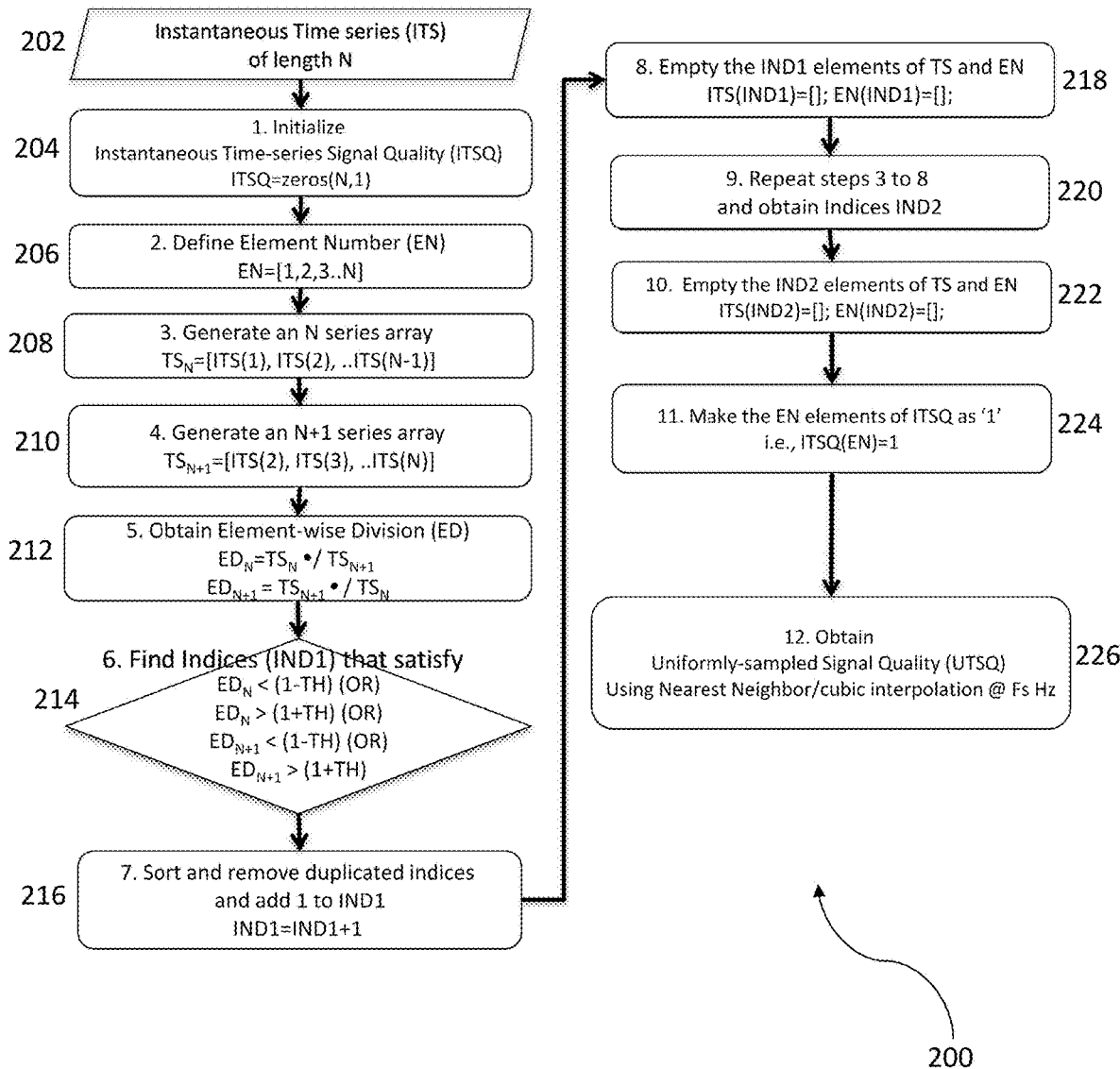
FIG. 2 illustrates a method of determining a Time Series Signal Quality (TSQ) of a cardiovascular time series in accordance with a first embodiment.

FIG. 2 illustrates a method 200 of determining a Time Series Signal Quality (TSQ) of a cardiovascular time series in accordance with a first embodiment. In FIG. 2, the wireless sensor device 100 is attached to a user to measure various cardiovascular signals (e.g. an ECG signal). An instantaneous time series (ITS) of length N (number of values) is fed as an input to a first process algorithm by the wireless sensor device 100, via step 202. The output of the first process algorithm, Instantaneous Time Series Signal Quality (ITSQ), is initialized by using a N×1 vector with N number of zeros to predefine an ITSQ value as corrupted denoted by 0 values per the equation ITSQ=zeros(N,1), where the N number of rows are all 0 values, via step 204. An Element Number (EN) is defined as EN=[1, 2, 3 . . . N] by using a N×1 vector that assigns a relative position of the elements in the ITS, via step 206.

In FIG. 2, an N series array ($TS_N$) is generated by eliminating the last element of the ITS and making a new vector where $TS_N$=[ITS(1), ITS(2) . . . ITS(N−1)], via step 208. An N+1 series array ($TS_{N+1}$) is generated by eliminating the first element of the ITS and making a new vector where $TS_{N+1}$=[ITS(2), ITS(3) . . . ITS(N)], via step 210. Element-wise division (ED) is obtained between the two arrays $TS_N$ and $TS_{N+1}$ per the equations $ED_N = TS_N \cdot / TS_{N+1}$ and $ED_{N+1} = TS_{N+1} \cdot / TS_N$, via step 212.

In FIG. 2, indices (IND1) are found that satisfy any of the equations $ED_N < (1-TH)$, $ED_N > (1+TH)$, $ED_{N+1} < (1-TH)$, or $ED_{N+1} > (1+TH)$ where TH equals a threshold for artifact detection that is either predefined by the user or determined from the cardiovascular signal, via step 214. The indices IND1 are sorted and added with 1 (e.g., IND1=IND1+1) to compensate for the division between the N and N+1 series arrays, via step 216. The element numbers EN corresponding to the indices IND1 are the potential artifact candidates. Hence, the IND1 elements of the ITS and element number EN series that offer the relative position of time series values of the ITS are removed per the equation ITS(IND1)=[ ]; EN(IND1)=[ ], via step 218.

Steps 208 to 218 are repeated to obtain indices (IND2), via step 220. The potential artifact candidates given by the indices IND2 are removed from the ITS and EN series per the equation ITS(IND2)=[ ]; EN(IND2)=[ ], via step 222. The elements of ITS that remain represent a cleaner instantaneous time series with reduced artifacts. The remaining elements of EN represent relative positions of the original input time series that correspond to clean data.

In FIG. 2, the remaining EN elements of the Instantaneous Time Series Signal Quality (ITSQ) array are set to 1 per the equation ITSQ(EN)=1 so that the ITSQ array includes both 0 and 1 values that correspond to corrupted (0 values) and clean (1 values) data, respectively, via step 224. The modified ITSQ array from step 224 represents one form of an algorithmic output of the method 200. The ITSQ array is initially predefined with zeros of length N×1, per step 204, and then the EN indices of ITSQ are changed to 1 values, per step 224, so the modified ITSQ array includes both 0 and 1 values indicating corrupt and clean values, respectively.

The time course of the modified ITSQ array from step 224 is the same as the ITS and is either a beat number or an instantaneous time denoting the beat or cardiac cycle. If the ITS is generated with respect to beat number, the modified ITSQ array will also be based on beat number. If the time course of the ITS is given with respect to instantaneous time sequence, the modified ITSQ array will also be non-uniformly spaced according to instantaneous time samples that are determined by the incidence of non-uniform cardiac cycles.

In order to obtain a Uniformly-Sampled Signal Quality (UTSQ) as another form of the algorithmic output of the method 200 at a user-defined uniform sampling rate of Fs Hertz (Hz) (e.g. 4 Hz), interpolation techniques are performed between the ITSQ values of the ITSQ array and the respective instantaneous time sequence for the ITS, via step 226. In one embodiment, nearest neighbor interpolation is utilized which offers binary values (either 0 or 1) as a quality estimate and in another embodiment, cubic interpolation is utilized which offers values between 0 and 1 as a quality estimate.

Figure 3:
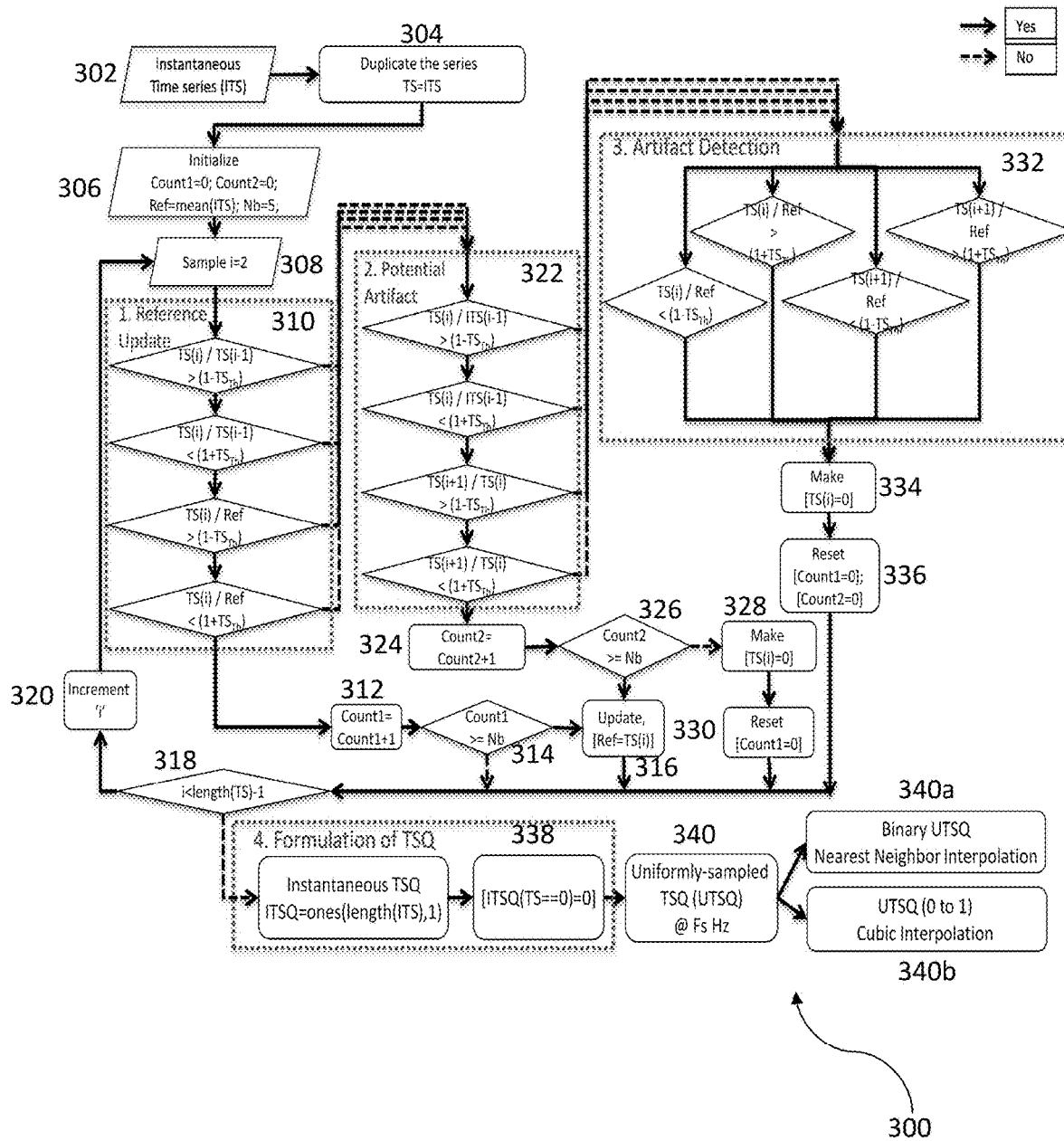
FIG. 3 illustrates a method of determining a Time Series Signal Quality (TSQ) of a cardiovascular time series in accordance with a second embodiment.

FIG. 3 illustrates a method 300 of determining a Time Series Signal Quality (TSQ) of a cardiovascular time series in accordance with a second embodiment. In FIG. 3, the wireless sensor device 100 is attached to a user to measure various cardiovascular signals (e.g. an ECG signal) and generate instantaneous time series (ITS). In FIG. 3, the abbreviation TS is a temporary array as a copy of the instantaneous time series (ITS); Nb is the number of normal consecutive beats; Count1 is a counter that tracks the normal values with reference to Nb; Count2 is a counter that tracks artifact values with reference to Nb; Ref is a reference value that changes continuously; i is a sample number; $TS_{Th}$ is an artifact threshold determined from signal variability; and Fs is a resampling frequency (Hz).

The instantaneous time series (ITS) of length N (number of values) is detected by the wireless sensor device 100, via step 302. The ITS is duplicated to generate TS by making a copy of the instantaneous time series and saving the copy as a new vector, via step 304. Two counters Count1 and Count2 are set to 0 and an initial reference value (Ref) is calculated as a mean of the entire time series ITS, via step 306. In one embodiment, the Nb value is set to 5 beats.

In FIG. 3, a second process algorithm loops through values of the ITS one-by-one and determines each value as either clean or corrupted data and subsequently generates an ITSQ series with 1 and 0 values to represent clean and corrupt values, respectively. The second process algorithm first considers the second sample of the ITS as current value sample (e.g., i=2), via step 308. The reference value is updated per the satisfaction of four conditions where i refers to a current value sample, i−1 refers to a previous value, and i+1 refers to a next value, via block 310.

The four conditions of block 310 are represented per the equations: a) $TS(i)/TS(i-1)>(1-TS_{Th})$, b) $TS(i)/TS(i-1)<(1+TS_{Th})$, c) $TS(i)/Ref>(1-TS_{Th})$, and d) $TS(i)/Ref<(1+TS_{Th})$. The four conditions of block 310 compare the present and previous values of the time series copy TS with respect to the boundaries of the normal threshold ($1-TS_{Th}$ and $1+TS_{Th}$), where $TS_{Th}$ is an artifact threshold value that can be predefined by the user or determined from the cardiovascular signal.

In FIG. 3, if all four conditions are satisfied via block 310, counter 1 is incremented per the equation Count1=Count1+1, via step 312, and then if Count1 satisfies the equation Count1>=Nb, via step 314, the reference value (Ref) is updated according to the current time series value TS(i) per the equation Ref=TS(i), via step 316. If any of the four conditions of block 310 are not satisfied, a second set of four conditions are compared that involve the present and the next values of the time series copy TS and the previous value of original time series ITS to identify potential motion artifacts followed by a previously declared artifact event, via block 322.

The four conditions of block 322 are represented per the equations: a) $TS(i)/ITS(i-1)>(1-TS_{Th})$, b) $TS(i)/ITS(i-1)<(1+TS_{Th})$, c) $TS(i+1)/TS(i)>(1-TS_{Th})$, and d) $TS(i+1)/TS(i)<(1+TS_{Th})$. In the first two conditions, the previous values (i−1) are taken from the original time series ITS instead of the time series copy TS because the previous value of TS could be "0" if it had been declared as corrupt during the last loop.

Block 322 identifies an episode of certain time series values followed by an artifact event that may be within the artifact threshold boundaries when 3 successive values are compared and thus may resemble normal values but could be "corrupted" artifact values. If the length of the consecutive time series values that satisfy the four conditions of block 322 is greater than Nb (the number of normal consecutive beats), then the identified time series values are denoted as normal values, otherwise the identified time series values are determined to be artifact values.

In FIG. 3, if all four conditions are satisfied via block 322, counter 2 is incremented per the equation Count2=Count2+1, via step 324, and then if Count2 satisfies the equation Count2>=Nb, via step 326, the reference value (Ref) is updated as the current time series value TS(i), via step 316. If Count2 is not greater than or equal to Nb, then TS(i) is determined to be an artifact and set to 0, via step 328, and Count1 is reset to 0, via step 330. If any of the four conditions of block 322 are not satisfied, a third set of four conditions are compared, via block 332.

In FIG. 3, the four conditions of block 332 are represented per the equations: a) $TS(i)/Ref<(1-TS_{Th})$, b) $TS(i)/Ref>(1+TS_{Th})$, c) $TS(i+1)/Ref<(1-TS_{Th})$, and d) $TS(i+1)/Ref>(1+TS_{Th})$. The four conditions of block 332 involve comparing the relationships between present (i) or next (i+1) time series values to the reference value Ref. If any of the four conditions of block 332 are satisfied, the current value sample (i) is confirmed to be an artifact and the current value of the time series copy TS is changed to 0 per the equation TS(i)=0, via step 334, and both counters are reset as Count1=0 and Count2=0, via step 336.

After any of steps 316, 330, 336 and when Count1 is not determined to be greater than or equal to Nb per step 314, the current sample i is compared to the length of TS minus 1 per the equation i<length(TS)−1, via step 318. If the current value sample (i) does not satisfy the condition in step 318 (e.g. i is not less than the length(TS)−1), then the current value sample is a penultimate value of the whole time series and a looping process of the method 300 for artifact detection is complete. Therefore, the TSQ is formulated based on zero elements generated in the temporary array TS during stages of artifact detection, via block 338. If i is less than length(TS)−1, then i is incremented, via step 320, and the looping process of the method 300 returns back to block 310 to start the calculations again.

For the formulation of ITSQ, the ITSQ time series is first predefined with all 1 values of length ITS per the equation ITSQ=ones(length(ITS),1) and then indices of a modified time series TS with 0 values are found and the indices values of the ITSQ time series are set to 0 per the equation ITSQ(TS==0)=0, via block 338. The modified ITSQ array from block 338 includes both 0 and 1 values that correspond to corrupted (0 values) and clean (1 values) data, respectively. The modified ITSQ array from block 338 represents one form of an algorithmic output of the method 300.

The time course of the ITSQ array from block 338 is the same as the ITS and is either a beat number or an instantaneous time denoting the beat or cardiac cycle. If the ITS is generated with respect to beat number, the ITSQ array will also be based on beat number. If the time course of the ITS is given with respect to instantaneous time sequence, the ITSQ array will also be non-uniformly spaced according to instantaneous time samples that are determined by the incidence of non-uniform cardiac cycles.

Once again, in order to obtain a Uniformly-Sampled Signal Quality (UTSQ) as another form of the algorithmic output of the method 300 at a user-defined uniform sampling rate of Fs Hertz (Hz) (e.g. 4 Hz), interpolation techniques are performed between the ITSQ values of the ITSQ array and the respective instantaneous time sequence for the ITS, via step 340. In one embodiment, nearest neighbor interpolation is utilized, via step 340a, which offers binary values (either 0 or 1) as a quality estimate and in another embodiment, cubic interpolation is utilized, via step 340b, which offers values between 0 and 1 as a quality estimate.

In one embodiment, the artifact threshold value (TH) is predefined as 20% using typical RR and PP intervals thereby resulting in a variability independent TH value. In another embodiment, cardiovascular time series metrics such as R-wave amplitude (RWA) are utilized to determine TH per the equation TH=(2*SD)/(Percentile Difference Between 95% and 5%)*100 where SD refers to the standard deviation and the lower and upper limits of TH are set to be 25% and 75% respectively thereby resulting in a variability dependent TH value.

If an input time series is completely clean and considered as Gaussian, the percentile difference between 95% and 5% measures dispersion of a probability distribution of the input time series which will be approximately 4*SD. For such an ideal input time series, the artifact threshold (TH) is calculated per the equation TH≅(2*SD)/((4*SD)*100≅50%. The practical time series inputs may not be completely clean and may have artifacts. Thus, a probability distribution of the practical time series inputs is not a perfect Gaussian and varies based on the presence of artifacts in the time series which affects the computation of TH. The selection of upper and lower limits of TH between 25% and 75% is arbitrary. Thus, in this embodiment, as the artifact threshold value is derived based on signal variability, artifact detection is customizable for individual recording and user personalization.

In one embodiment, a method determines a signal quality metric of a cardiovascular time series utilizing a wireless sensor device by determining subsequent values of the cardiovascular time series and by comparing the determined subsequent values to a threshold value. The determination of subsequent values performs array-based calculations on the subsequent values of the cardiovascular time series. The comparing step determines whether each individual time series value of the cardiovascular time series is a normal "clean" value or an artifact "corrupt" value. In this embodiment, the threshold value is determined from signal variability of the cardiovascular time series and the subsequent values are determined from any of subsequent beats and cardiac cycles of the cardiovascular time series.

In another embodiment, the method includes comparing the determined subsequent time periods to a reference value in addition to the threshold value using a decision tree model to determine whether each individual time series value of the cardiovascular time series is a normal "clean" value or an artifact "corrupt" value. The reference value is continuously updated within a predetermined window represented by a number of normal consecutive beats (Nb) using a first set of conditions.

In this embodiment, the method includes flagging at least one individual time series value of the cardiovascular time series if a second set of conditions is satisfied and identifying potential artifacts in the cardiovascular time series by comparing the at least one flagged individual time series value to the Nb. In one embodiment, if the at least one flagged individual time series value is greater than Nb, then the at least one flagged individual time series value is determined to be a normal value, but if the at least one flagged individual time series value is less than Nb, then the at least one flagged individual time series value is determined to be a potential artifact value.

In this embodiment, the potential artifact value is confirmed as an artifact value if any of a third set of conditions is satisfied. In one embodiment, the method includes updating the cardiovascular time series with 0 values for confirmed artifact values and with 1 values for confirmed normal values. In one embodiment, the method includes formulating, by the wireless sensor device, the signal quality metric utilizing the updated cardiovascular time series and uniformly sampling the signal quality metric using any of nearest neighbor and cubic interpolation.

As above described, the method and system allow for determining a signal quality metric for all types of cardiovascular time series that have been derived by a wireless sensor device using detected physiological signals (e.g. ECG signal). The signal quality metric is determined by the wireless sensor device for the cardiovascular time series at a beat level as well as at a uniform sampling rate of Fs Hz (e.g. 1 to 4 Hz). The algorithmic processes utilized by the wireless sensor device per the methods 200 and 300 identify both physical and physiological artifacts in secondary signal levels that assist in correct interpretation in further data analysis. The decisions regarding clean or corrupt values generated from both algorithmic processes are used to generate a concurrent time series signal quality metric that indicates the quality of the cardiovascular time series.

In one embodiment, by detecting a cardiovascular signal and deriving an associated cardiovascular time series from the detected cardiovascular signal, the wireless sensor device calculates a Time Series Signal Quality (TSQ) metric by analyzing subsequent beats or cardiac cycles and comparing data values of the analyzed beats/cycles to a threshold value that is determined from the normal variability of the cardiovascular time series utilizing a first algorithmic process (method 200). In another embodiment, the wireless sensor device calculates a Time Series Signal Quality (TSQ) from the associated cardiovascular time series by comparing data values of the analyzed beats/cycles to both a reference value and the threshold value utilizing a second algorithmic process.

A method and system for determining a signal quality metric of a cardiovascular time series that is detected by a wireless sensor device have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for determining a signal quality metric of a cardiovascular time series utilizing a wireless sensor device, the method comprising:
   determining subsequent values of the cardiovascular time series within a pre-determined window;
   comparing the determined subsequent values of a pre-determined window to a reference value and a threshold value to determine if each individual time series value of the cardiovascular time series is a normal value or an artifact value and to produce the signal quality metric, wherein an initial reference value (Ref) is calculated as a mean of the entire time series instantaneous time series (ITS) and the reference value is updated as a current time series value within the pre-determined window using each individual time series value of the cardiovascular time series that is determined to be a normal value;
   performing interpolation on the signal quality metric to determine a uniformly sampled signal quality metric; and
   relaying, using a transmitter, the uniformly sampled signal quality metric to another user or device.

2. The method of claim 1, wherein the threshold value is determined from signal variability of the cardiovascular time series.

3. The method of claim 1, wherein the subsequent values of the cardiovascular time series are determined by performing array-based calculations on the subsequent values of the cardiovascular time series.

4. The method of claim 1, wherein
   comparing the determined subsequent values to the reference value and the threshold value to determine whether each individual time series value of the cardiovascular time series is a normal value or an artifact value uses a decision tree model.

5. The method of claim 4, wherein the predetermined window is represented by a number of normal consecutive beats (Nb) using a first set of conditions.

6. The method of claim 5, further comprising:
   flagging at least one individual time series value of the cardiovascular time series if a second set of conditions is satisfied; and
   identifying potential artifacts in the cardiovascular time series by comparing the at least one flagged individual time series value to the Nb.

7. The method of claim 6, wherein if the at least one flagged individual time series value is greater than Nb, then the at least one flagged individual time series value is determined to be a normal value, but if the at least one flagged individual time series value is less than Nb, then the at least one flagged individual time series value is determined to be a potential artifact value.

8. The method of claim 7, wherein the potential artifact value is confirmed as an artifact value if any of a third set of conditions is satisfied.

9. The method of claim 8, further comprising:
   updating the cardiovascular time series with 0 values for confirmed artifact values and with 1 values for confirmed normal values.

10. The method of claim 9, further comprising:
    formulating the signal quality metric utilizing the updated cardiovascular time series; and
    uniformly sampling the signal quality metric using any of nearest neighbor and cubic interpolation.

11. A wireless sensor device for determining a signal quality metric of a cardiovascular time series, comprising:
    a processor; and
    a memory coupled to the processor, wherein the memory includes an application that, when executed by the processor, causes the processor to:
      determine subsequent values of the cardiovascular time series of a pre-determined window;
    compare the determined subsequent values of a pre-determined window to a reference value and a threshold value to determine if each individual time series value of the cardiovascular time series is a normal value or an artifact value and to produce the signal quality metric, wherein an initial reference value (Ref) is calculated as a mean of the entire time series instantaneous time series (ITS) and the reference value is updated as a current time series value within the pre-determined window using each individual time series value of the cardiovascular time series that is determined to be a normal value;
    perform interpolation on the signal quality metric to determine a uniformly sampled signal quality metric; and
    a transmitter to relay the uniformly sampled signal quality metric to another user or device.

12. The system of claim 11, wherein the processor determines the subsequent values of the cardiovascular time series by performing array-based calculations.

13. The system of claim 11, wherein the predetermined window is represented by a number of normal consecutive beats (Nb) using a first set of conditions.

14. The system of claim 13, wherein the application, when executed by the processor, further causes the processor to:
    flag at least one individual time series value of the cardiovascular time series if a second set of conditions is satisfied; and
    identify potential artifacts in the cardiovascular time series by comparing the at least one flagged individual time series value to the Nb.

15. The system of claim 14, wherein if the at least one flagged individual time series value is greater than Nb, then the at least one flagged individual time series value is determined to be a normal value, but if the at least one flagged individual time series value is less than Nb, then the at least one flagged individual time series value is determined to be a potential artifact value.

16. The system of claim 15, wherein the potential artifact value is confirmed as an artifact value if any of a third set of conditions is satisfied.

17. The system of claim 16, wherein the application, when executed by the processor, further causes the processor to:
update the cardiovascular time series with 0 values for confirmed artifact values and with 1 values for confirmed normal values.

18. The system of claim 17, wherein the application, when executed by the processor, further causes the processor to:
formulate the signal quality metric utilizing the updated cardiovascular time series; and
uniformly sample the signal quality metric using any of nearest neighbor and cubic interpolation.

* * * * *